(12) United States Patent
Jackson, III

(10) Patent No.: US 9,561,086 B2
(45) Date of Patent: Feb. 7, 2017

(54) ACETABULAR COMPONENT ANTEVERSION AND ABDUCTION MEASUREMENT SYSTEM AND METHOD

(71) Applicant: J. Benjamin Jackson, III, Salt Lake City, UT (US)

(72) Inventor: J. Benjamin Jackson, III, Salt Lake City, UT (US)

(73) Assignee: J. Benjamin Jackson, III, Irmo, SC (US)

( * ) Notice: Subject to any disclaimer, the term of this patent is extended or adjusted under 35 U.S.C. 154(b) by 0 days.

(21) Appl. No.: 14/704,040

(22) Filed: May 5, 2015

(65) Prior Publication Data

US 2015/0313724 A1 Nov. 5, 2015

Related U.S. Application Data

(60) Provisional application No. 61/988,719, filed on May 5, 2014.

(51) Int. Cl.
*A61F 2/32* (2006.01)
*A61F 2/46* (2006.01)
*A61B 19/00* (2006.01)
*A61F 2/34* (2006.01)

(52) U.S. Cl.
CPC ............... *A61B 90/39* (2016.02); *A61B 19/54* (2013.01); *A61F 2/34* (2013.01); *A61F 2/46* (2013.01); *A61F 2/4609* (2013.01); *A61F 2/4657* (2013.01); *A61B 2019/5466* (2013.01); *A61B 2090/3966* (2016.02); *A61F 2002/345* (2013.01); *A61F 2002/4668* (2013.01); *A61F 2002/4687* (2013.01)

(58) Field of Classification Search
CPC ............... A61F 2/34; A61F 2002/3008; A61F 2002/3451
See application file for complete search history.

(56) References Cited

U.S. PATENT DOCUMENTS

| | | | |
|---|---|---|---|
| 4,224,698 A | 9/1980 | Hopson | |
| 5,405,402 A | 4/1995 | Dye et al. | |
| 2004/0117028 A1 | 6/2004 | Iversen | |
| 2005/0246020 A1 | 11/2005 | Southworth | |
| 2014/0018932 A1 | 1/2014 | McMahon et al. | |
| 2014/0276889 A1 | 9/2014 | Head et al. | |

FOREIGN PATENT DOCUMENTS

GB 2134360 A 8/1984

*Primary Examiner* — Brian Dukert
(74) *Attorney, Agent, or Firm* — Clements Bernard PLLC; Christopher L. Bernard; Lawrence A. Baratta, Jr.

(57) ABSTRACT

An acetabular component anteversion and abduction measurement system, comprising: an acetabular component; one or more radiopaque guide lines disposed on or adjacent to a posterior surface of the acetabular component; and one or more radiopaque guide lines disposed on or adjacent to an anterior surface of the acetabular component; wherein predetermined alignment of selected of the one or more anterior guide lines with selected of the one or more posterior guide lines under intra-operative fluoroscopy or radiography indicates proper surgical alignment of the acetabular component within the anatomy of a patient. Proper surgical alignment means that the acetabular component is not retroverted or overly anteverted or abducted within the anatomy of the patient.

16 Claims, 10 Drawing Sheets

ACETABULAR COMPONENT ANTEVERSION AND ABDUCTION MEASUREMENT SYSTEM AND METHOD

CROSS-REFERENCE TO RELATED APPLICATION

The present patent application/patent claims the benefit of priority of co-pending U.S. Provisional Patent Application No. 61/988,719, filed on May 5, 2014, and entitled "ACETABULAR COMPONENT ANTEVERSION MEASUREMENT SYSTEM AND METHOD," the contents of which are incorporated in full by reference herein.

FIELD OF THE INVENTION

The present invention relates generally to a surgical system and method for performing hip surgery. More specifically, the present invention relates to an acetabular component anteversion and abduction measurement system and method.

BACKGROUND OF THE INVENTION

In partial or total minimally invasive (MIS) hip surgery, a surgeon operates through an incision of about 10 cm or less without imparting problematic anatomical forces or compromising component positioning. Conventionally, an open approach has utilized an incision of about 15-30 cm, leading to more tissue damage, more blood loss, more post-operative pain, a longer hospital stay, and a delayed return to work and other functional activities.

One downside to MIS hip surgery, however, is that conventional instruments can damage soft tissues when used through a small incision, and there is a risk of implanting components incorrectly, especially the acetabular component, which may inadvertently be anteverted or abducted, such that the hip joint is in an improper orientation and is "open" (overly anteverted) or "closed" (retroverted) too much. FIG. 1 is a series of images illustrating an example of a retroverted acetabular component (on the left) and an overly anteverted acetabular component (on the right).

Anteversion and abduction of the acetabular component are very difficult to judge intra-operatively, and are often done post-operatively using various computerized alignment measurement systems. Thus, the present invention provides systems and methods that utilize intra-operative fluoroscopy and/or intra-operative radiographs and visualizable guide lines to measure the anteversion or abduction of the acetabular component. The systems and methods of the present invention find particular applicability in a direct anterior (DA) approach to the hip, as well as other approaches, as will best be appreciated by those of ordinary skill in the art.

BRIEF SUMMARY OF THE INVENTION

Again, in various exemplary embodiments, the present invention provides systems and methods that utilize intra-operative fluoroscopy and/or intra-operative radiographs and visualizable guide lines to measure the anteversion or abduction of the acetabular component. The systems and methods of the present invention find particular applicability in a direct anterior (DA) approach to the hip, as well as other approaches, as will best be appreciated by those of ordinary skill in the art.

In one exemplary embodiment, the present invention provides an acetabular component anteversion and abduction measurement system, comprising: an acetabular component; one or more radiopaque guide lines disposed on a posterior surface of the acetabular component; and one or more radiopaque guide lines disposed on or formed by an anterior surface of the acetabular component; wherein predetermined alignment of selected of the one or more anterior guide lines with selected of the one or more posterior guide lines under intra-operative fluoroscopy indicates proper surgical alignment of the acetabular component within the anatomy of a patient. The acetabular component comprises a hollow, substantially hemispherical structure. Preferably, the one or more posterior guide lines comprise a plurality of posterior guide lines. Preferably, the one or more anterior guide lines comprise one anterior guide line. The guide lines are partially or wholly concentrically arranged about an interior or exterior surface of the acetabular component. Proper surgical alignment means that the acetabular component is not retroverted or overly anteverted or abducted within the anatomy of the patient.

In another exemplary embodiment, the present invention provides an acetabular component anteversion and abduction measurement system, comprising: an acetabular component; one or more radiopaque guide lines disposed adjacent to a posterior surface of the acetabular component; and one or more radiopaque guide lines disposed adjacent to an anterior surface of the acetabular component; wherein predetermined alignment of selected of the one or more anterior guide lines with selected of the one or more posterior guide lines under intra-operative fluoroscopy indicates proper surgical alignment of the acetabular component within the anatomy of a patient. The acetabular component comprises a hollow, substantially hemispherical structure. Preferably, the one or more posterior guide lines comprise a plurality of posterior guide lines. Preferably, the one or more anterior guide lines comprise one anterior guide line. The guide lines are partially or wholly concentrically arranged about an interior or exterior surface of the acetabular component. Proper surgical alignment means that the acetabular component is not retroverted or overly anteverted or abducted within the anatomy of the patient. In this exemplary embodiment, the guide lines are disposed on an interior or exterior surface of a conformal insert that is selectively disposed within the acetabular component.

In a further exemplary embodiment, the present invention provides an acetabular component anteversion and abduction measurement method, comprising: providing an acetabular component; providing one or more radiopaque guide lines disposed on or adjacent to a posterior surface of the acetabular component; and providing one or more radiopaque guide lines disposed on or formed by or disposed adjacent to an anterior surface of the acetabular component; wherein predetermined alignment of selected of the one or more anterior guide lines with selected of the one or more posterior guide lines under intra-operative fluoroscopy indicates proper surgical alignment of the acetabular component within the anatomy of a patient. The acetabular component comprises a hollow, substantially hemispherical structure. Preferably, the one or more posterior guide lines comprise a plurality of posterior guide lines. Preferably, the one or more anterior guide lines comprise one anterior guide line. The guide lines are partially or wholly concentrically arranged about an interior or exterior surface of the acetabular component. Proper surgical alignment means that the acetabular component is not retroverted or overly anteverted or abducted within the anatomy of the patient.

BRIEF DESCRIPTION OF THE DRAWINGS

The present invention is illustrated and described herein with reference to the various drawings, in which like reference numbers are used to denote like system components/ method steps, as appropriate, and in which.

DETAILED DESCRIPTION OF THE INVENTION

Figure 1:
FIG. 1 is a series of images illustrating an example of a retroverted acetabular component (on the left) and an overly anteverted acetabular component (on the right)

Again, in various exemplary embodiments, the present invention provides systems and methods that utilize intra-operative fluoroscopy and visualizable guide lines to measure the anteversion or abduction of the acetabular component. The systems and methods of the present invention find particular applicability in a direct anterior (DA) approach to the hip, as well as other approaches, as will best be appreciated by those of ordinary skill in the art. FIG. 1 is a series of images illustrating an example of a retroverted acetabular component (on the left) and an overly anteverted acetabular component (on the right).

Figure 2:
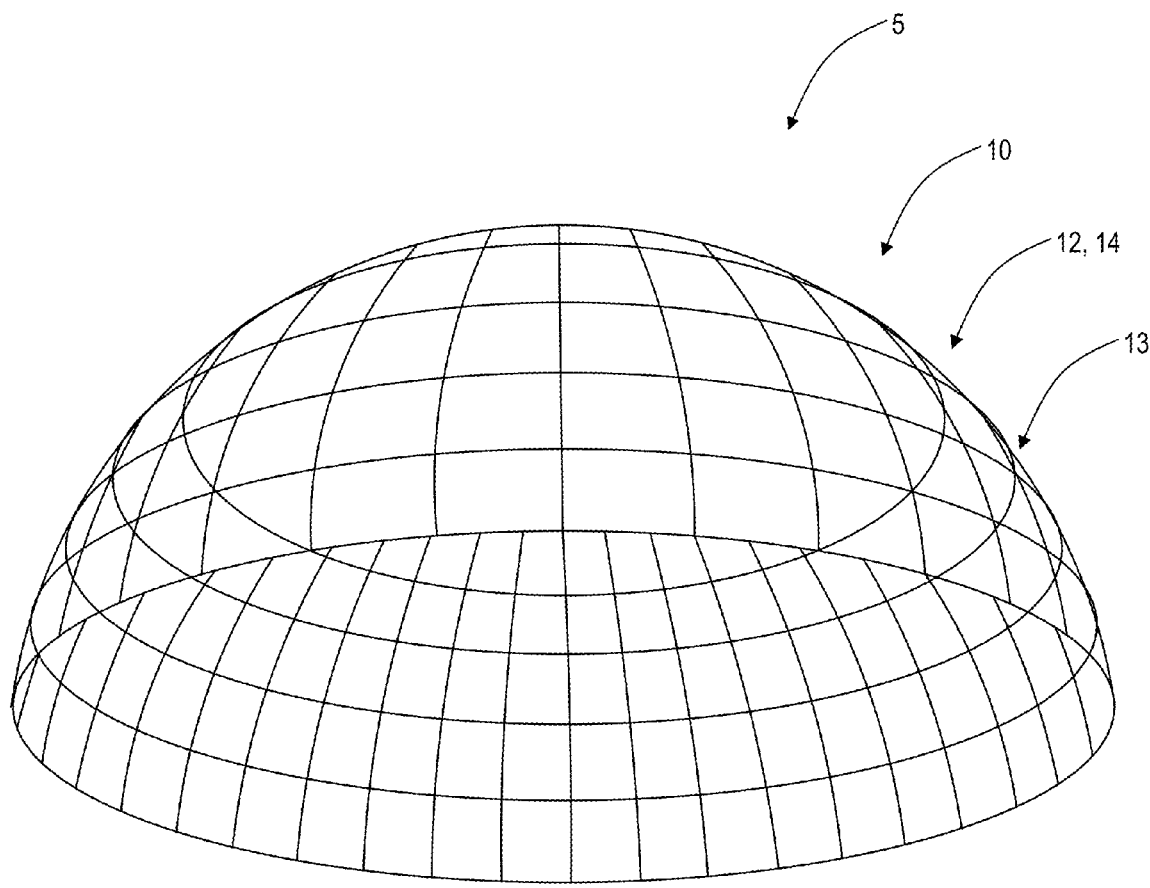
FIG. 2 is a schematic diagram illustrating one exemplary embodiment of the acetabular component anteversion and abduction measurement system of the present invention.
Figure 7:
FIG. 7 is an image illustrating an example of a properly aligned acetabular component using the acetabular component anteversion and abduction measurement system of the present invention.

FIG. 2 is a schematic diagram illustrating one exemplary embodiment of the acetabular component anteversion and abduction measurement system 5 of the present invention. In general, the acetabular component 10 consists of a conventional hollow hemispherical structure or the like that is manufactured from any suitable surgically-implantable material, such as a metal, metal alloy, or polymeric material. The acetabular component 10 may include any appropriate tool engaging and/or securement features, as is also conventional. In accordance with the present invention, the acetabular component 10 includes a plurality of partially or wholly concentrically-arranged guide lines 12, 14 that are visualizable under intra-operative fluoroscopy or the like. Optionally, the acetabular component 10 also includes a plurality of partially or wholly vertically-arranged guide lines 13 that are also visualizable under intra-operative fluoroscopy or the like. These guidelines 12, 14 may have any suitable spacing and are lined up in a predetermined manner, "front" to "back" during surgery to ensure a proper orientation of the acetabular component 10 during surgery, as is illustrated in FIG. 7. This ensures that the acetabular component 10 is not retroverted or overly anteverted or abducted. The guide lines 12, 14 may be manufactured into or printed on either the inner or the outer surface of the acetabular component 10, or may be disposed on a removable temporary liner in the acetabular component 10 and utilized during positioning of the acetabular component 10.

Figure 3:
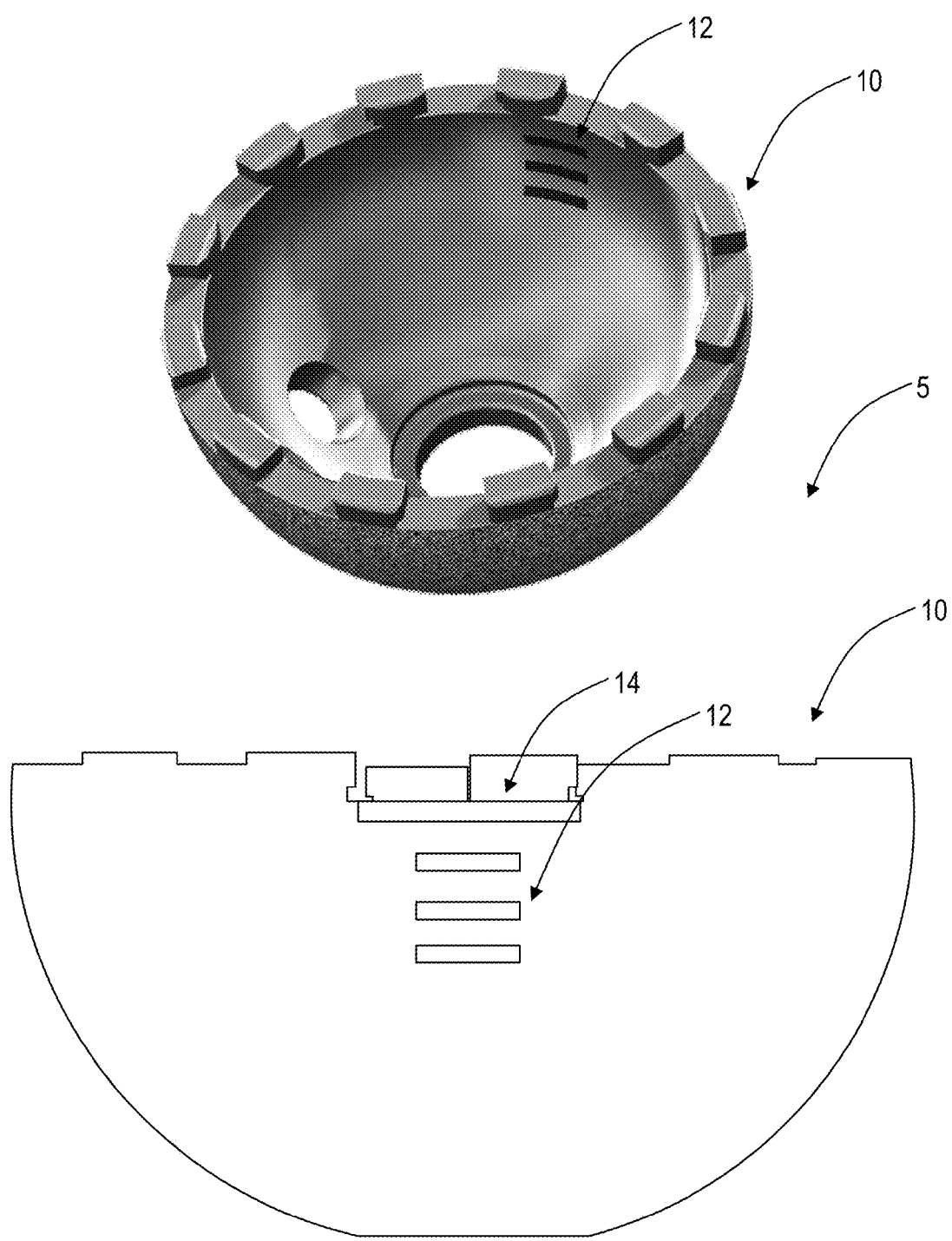
FIG. 3 is a perspective and planar view illustrating another exemplary embodiment of the acetabular component anteversion and abduction measurement system of the present invention, in an integrated configuration.
Figure 4:
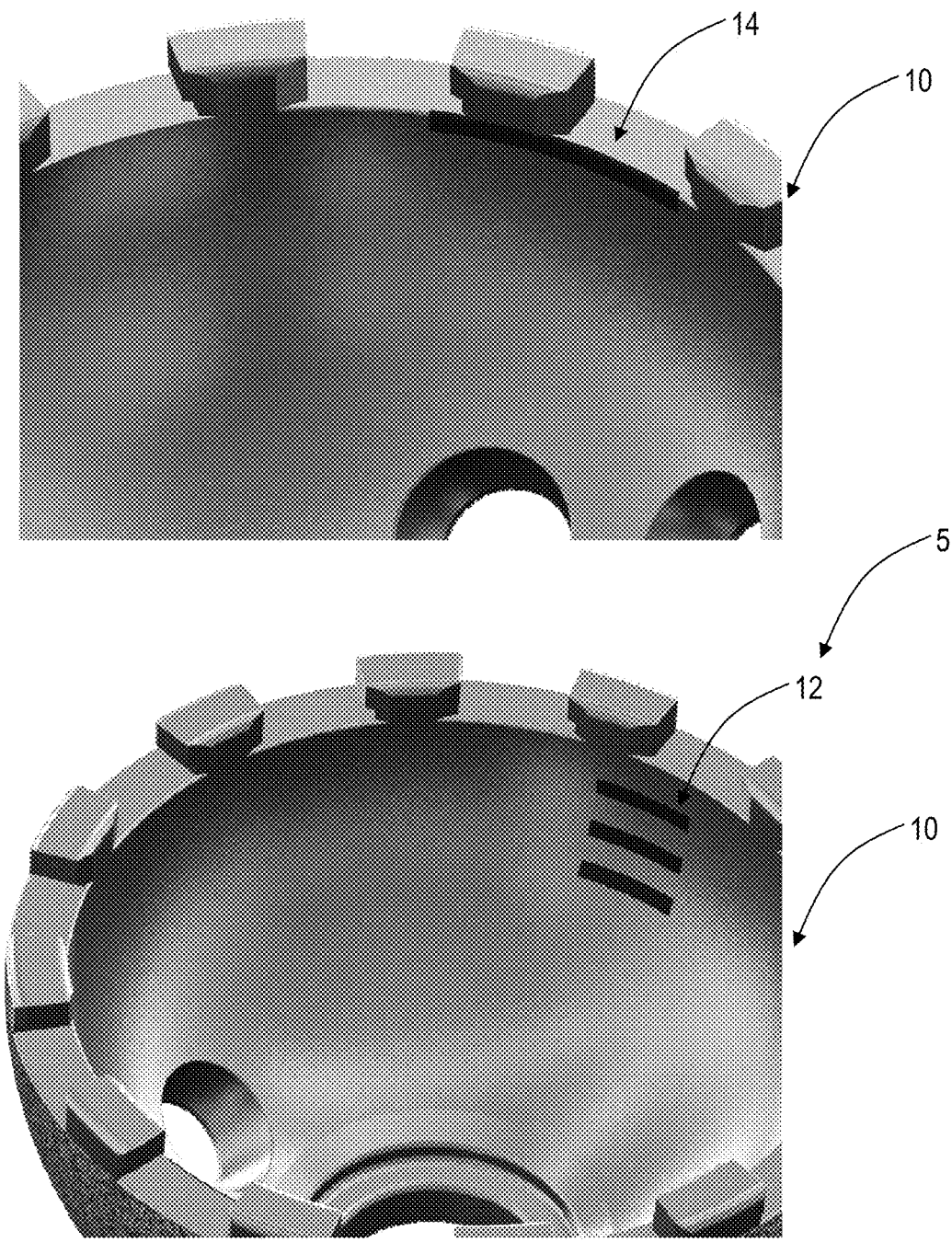
FIG. 4 is a series of perspective views illustrating another exemplary embodiment of the acetabular component anteversion and abduction measurement system of the present invention, in an integrated configuration.

FIGS. 3 and 4 are perspective and planar views illustrating another exemplary embodiment of the acetabular component anteversion and abduction measurement system 5 of the present invention, in an integrated configuration. Again, in general, the acetabular component 10 consists of a conventional hollow hemispherical structure or the like that is manufactured from any suitable surgically-implantable material, such as a metal, metal alloy, or polymeric material. The acetabular component 10 may include any appropriate tool engaging and/or securement features, as is also conventional. In accordance with the present invention, the acetabular component 10 includes a plurality of partially concentrically-arranged back guide lines 12 and one or more partially concentrically-arranged front guidelines 14 that are visualizable under intra-operative fluoroscopy or the like. Optionally, the acetabular component 10 also includes a plurality of partially or wholly vertically-arranged guide lines (not illustrated) that are also visualizable under intra-operative fluoroscopy or the like. These guidelines 12, 14 may have any suitable spacing and are lined up in a predetermined manner, "front" to "back" during surgery to ensure a proper orientation of the acetabular component 10 during surgery, again as is illustrated in FIG. 7. This ensures that the acetabular component 10 is not retroverted or overly anteverted or abducted. The guide lines 12, 14 may be manufactured into or printed on either the inner or the outer surface of the acetabular component 10.

Figure 5:
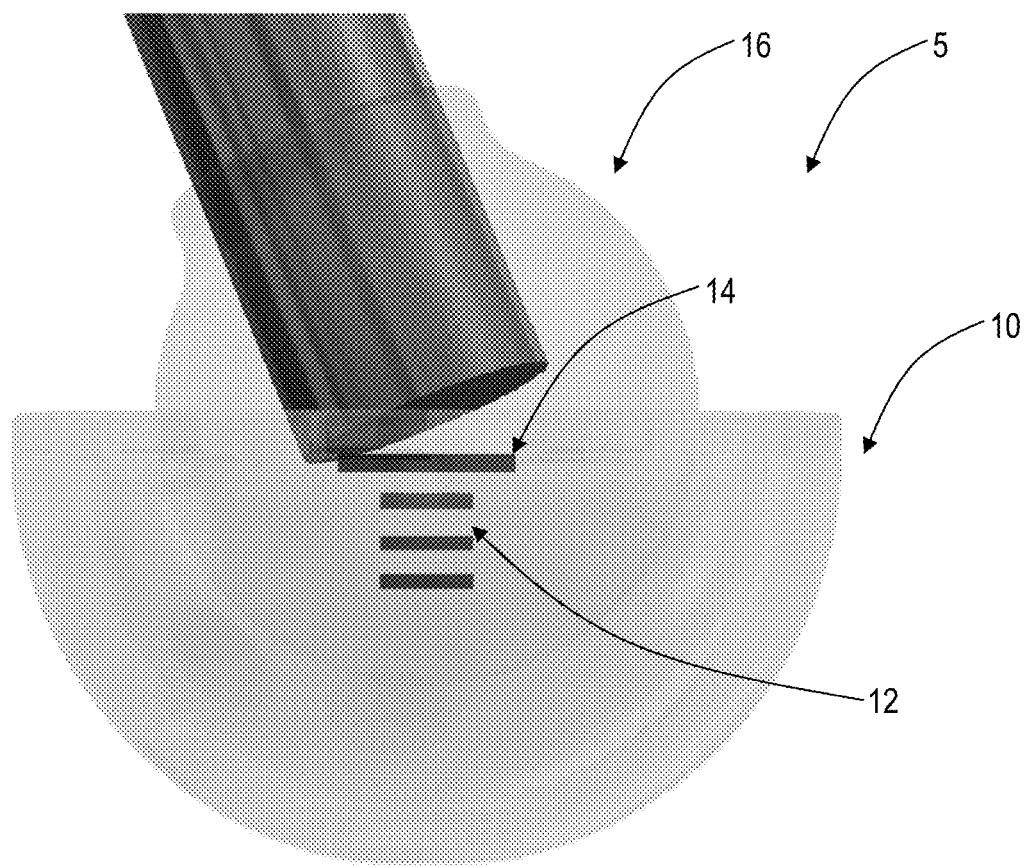
FIG. 5 is a planar view illustrating another exemplary embodiment of the acetabular component anteversion and abduction measurement system of the present invention, highlighting the use of an insertion/alignment tool.

FIG. 5 is a planar view illustrating another exemplary embodiment of the acetabular component anteversion and abduction measurement system 5 of the present invention, highlighting the use of an insertion/alignment tool 16. The insertion/alignment tool 16 is used to rotate, pivot, and otherwise orient the acetabular component 10 in a proper alignment using the guide lines 12, 14. This tool 16 may be integrated with the acetabular component 10 during insertion.

Figure 6:
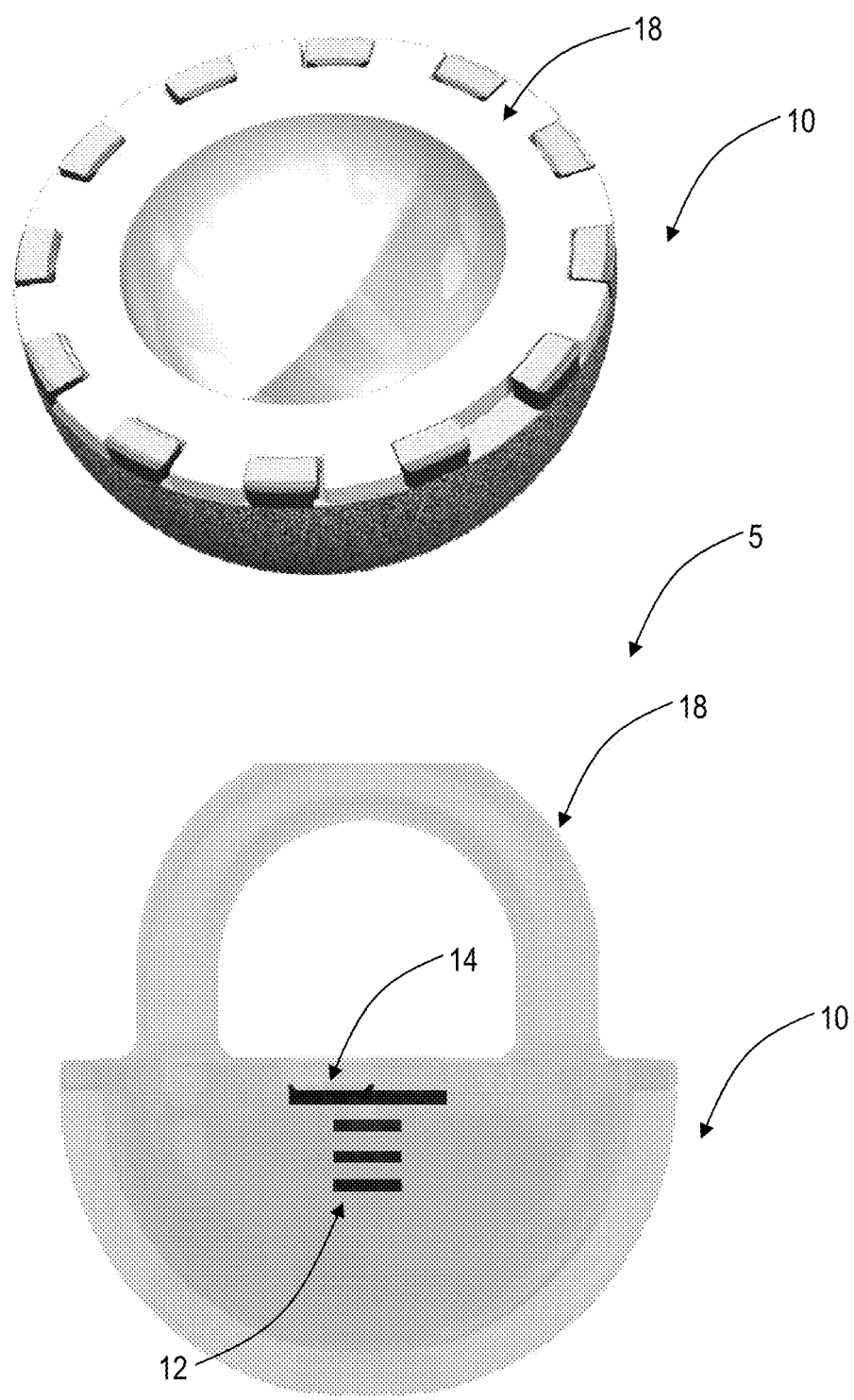
FIG. 6 is a perspective and planar view illustrating a further exemplary embodiment of the acetabular component anteversion and abduction measurement system of the present invention, in an insert configuration.

FIG. 6 is a perspective and planar view illustrating a further exemplary embodiment of the acetabular component anteversion and abduction measurement system 5 of the present invention, in an insert configuration. Again, in general, the acetabular component 10 consists of a conventional hollow hemispherical structure or the like that is manufactured from any suitable surgically-implantable material, such as a metal, metal alloy, or polymeric material. The acetabular component 10 may include any appropriate tool engaging and/or securement features, as is also conventional. In accordance with the present invention, the acetabular component 10 includes a plurality of partially concentrically-arranged back guide lines 12 and one or more partially concentrically-arranged front guidelines 14 that are visualizable under intra-operative fluoroscopy or the like. Optionally, the acetabular component 10 also includes a plurality of partially or wholly vertically-arranged guide lines (not illustrated) that are also visualizable under intra-operative fluoroscopy or the like. These guidelines 12, 14 may have any suitable spacing and are lined up in a predetermined manner, "front" to "back" during surgery to ensure a proper orientation of the acetabular component 10 during surgery, again as is illustrated in FIG. 7. This ensures that the acetabular component 10 is not retroverted or overly anteverted or abducted. In this exemplary embodiment, the guide lines 12, 14 are manufactured into or printed on either the inner or the outer surface of a permanent or removable insert 18 that is conformally disposed in the acetabular component 10. Optionally, this insert 18 is "keyed" such that its orientation is fixed with respect to the acetabular component 10.

Advantageously, the systems and methods of the present invention do not harm the acetabular component 10, are reliable, can be sterilized, can be used to measure abduction, are radiopaque, and can be used to measure anteversion of the acetabular component 10 from an intra-operative fluoroscopic or radiographic image. The acetabular component anteversion and abduction measurement system 5 includes calibrated guide lines 12, 14 that are disposed directly on the posterior surface or in a removable liner, such that when the anterior line is overlying the posterior calibrations, one can readily detect the anteversion or abduction of the component 10. These markers 12, 14 may either be placed inside the cup 10 on an insert 18 and then removed, or they can be imbedded into the component 10 itself. It should be noted that the anterior guide line(s) 14 may be longer or shorter than the posterior guide line(s) 12 (or otherwise differ) such that they may be distinguished during imaging and visualization.

Figure 8:
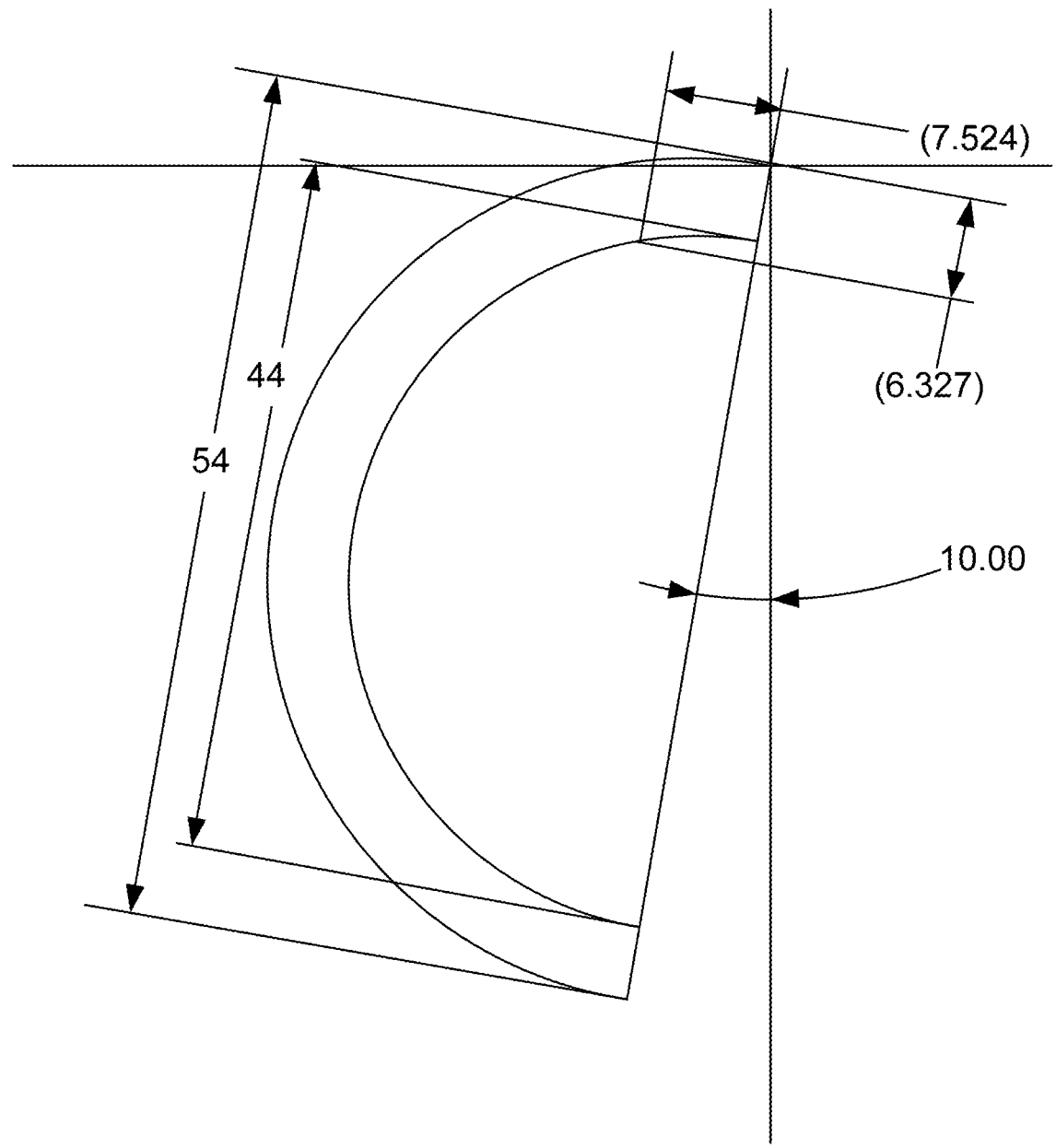
FIG. 8 is a schematic diagram illustrating one exemplary method for locating the posterior and anterior guide lines of the present invention.

FIG. 8 is a schematic diagram illustrating one exemplary method for locating the posterior and anterior guide lines of the present invention. For example, the size of the acetabular component may vary, but guidelines are generally placed at 10 degrees, 15 degrees, and 20 degrees from the lower edge of the acetabular component (for anteversion on the order of 40 degrees, 45 degrees, or 50 degrees).

Figure 9:
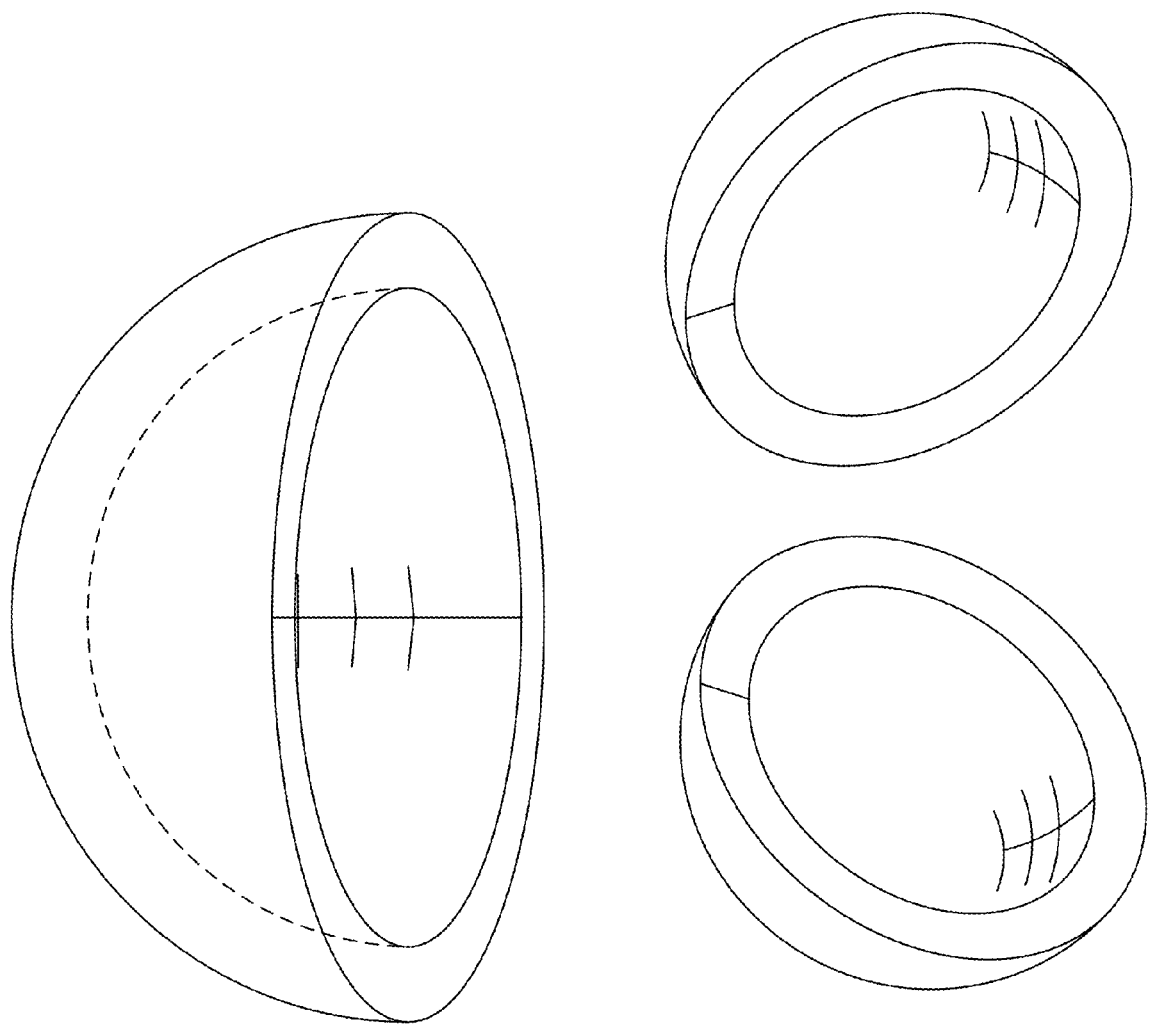
FIG. 9 is a series of perspective views illustrating a still further exemplary embodiment of the acetabular component anteversion and abduction measurement system of the present invention, in an integrated configuration.
Figure 10:
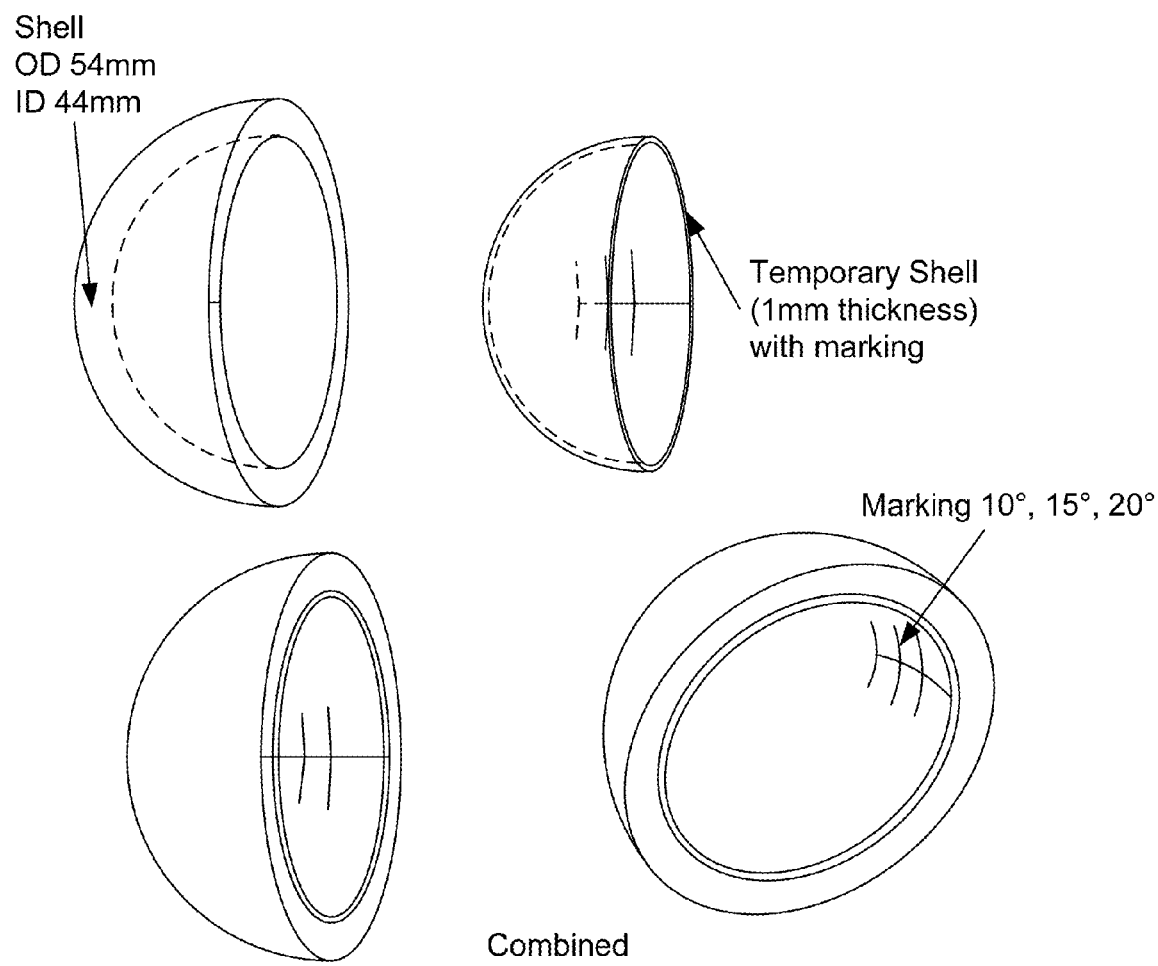
FIG. 10 is a series of perspective views illustrating a still further exemplary embodiment of the acetabular component anteversion and abduction measurement system of the present invention, in an insert configuration.

FIG. 9 is a series of perspective views illustrating a still further exemplary embodiment of the acetabular component anteversion and abduction measurement system of the present invention, in an integrated configuration. Similarly, FIG. 10 is a series of perspective views illustrating a still further exemplary embodiment of the acetabular component anteversion and abduction measurement system of the present invention, in an insert configuration. In these embodiments, concentric posterior guide lines are utilized, as well as a vertical posterior guide line. On the anterior side, the concentric guideline consists of the edge of the acetabular component itself, while the vertical guideline consists of a marking on the bottom edge of the acetabular component, as is illustrated and annotated.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An acetabular component anteversion and abduction measurement system, comprising:
an acetabular component;
a plurality of radiopaque guide lines disposed in a spaced apart relationship on a posterior surface of the acetabular component; and
one or more radiopaque guide lines disposed on or formed by an anterior surface of the acetabular component;
wherein at least one of the guide lines is aligned substantially perpendicular to others of the guide lines; and
wherein predetermined alignment of selected of the one or more anterior guide lines with selected of the plurality of posterior guide lines under intra-operative fluoroscopy indicates proper surgical alignment of the acetabular component within the anatomy of a patient.

2. The system of claim 1, wherein the acetabular component comprises a hollow, substantially hemispherical structure.

3. The system of claim 1, wherein the one or more anterior guide lines comprise one anterior guide line.

4. The system of claim 1, wherein the guide lines are partially or wholly concentrically arranged about an interior or exterior surface of the acetabular component.

5. The system of claim 1, wherein proper surgical alignment means that the acetabular component is not retroverted or overly anteverted or abducted within the anatomy of the patient.

6. An acetabular component anteversion and abduction measurement system, comprising:
an acetabular component;
a plurality of radiopaque guide lines disposed in a spaced apart relationship adjacent to a posterior surface of the acetabular component; and
one or more radiopaque guide lines disposed adjacent to an anterior surface of the acetabular component;
wherein at least one of the guide lines is aligned substantially perpendicular to others of the guide lines; and
wherein predetermined alignment of selected of the one or more anterior guide lines with selected of the plurality of posterior guide lines under intra-operative fluoroscopy indicates proper surgical alignment of the acetabular component within the anatomy of a patient.

7. The system of claim 6, wherein the acetabular component comprises a hollow, substantially hemispherical structure.

8. The system of claim 6, wherein the one or more anterior guide lines comprise one anterior guide line.

9. The system of claim 6, wherein the guide lines are partially or wholly concentrically arranged about an interior or exterior surface of the acetabular component.

10. The system of claim 6, wherein proper surgical alignment means that the acetabular component is not retroverted or overly anteverted or abducted within the anatomy of the patient.

11. The system of claim 6, further comprising a conformal insert that is selectively disposed within the acetabular component.

12. An acetabular component anteversion and abduction measurement method, comprising:
providing an acetabular component;
providing a plurality of radiopaque guide lines disposed in a spaced apart relationship on or adjacent to a posterior surface of the acetabular component; and
providing one or more radiopaque guide lines disposed on or formed by or disposed adjacent to an anterior surface of the acetabular component;
wherein at least one of the guide lines is aligned substantially perpendicular to others of the guide lines; and
wherein predetermined alignment of selected of the one or more anterior guide lines with selected of the plurality of posterior guide lines under intra-operative fluoroscopy indicates proper surgical alignment of the acetabular component within the anatomy of a patient.

13. The method of claim 12, wherein the acetabular component comprises a hollow, substantially hemispherical structure.

14. The method of claim 12, wherein the one or more anterior guide lines comprise one anterior guide line.

15. The method of claim 12, wherein the guide lines are partially or wholly concentrically arranged about an interior or exterior surface of the acetabular component.

16. The method of claim 12, wherein proper surgical alignment means that the acetabular component is not retroverted or overly anteverted or abducted within the anatomy of the patient.

* * * * *